United States Patent
Poisner

(10) Patent No.: US 7,854,703 B2
(45) Date of Patent: Dec. 21, 2010

(54) PERIPHERAL NEUROPATHY DETECTION

(75) Inventor: David Poisner, Carmichael, CA (US)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 11/860,846

(22) Filed: Sep. 25, 2007

(65) Prior Publication Data

US 2009/0082694 A1 Mar. 26, 2009

(51) Int. Cl.
*A61B 5/00* (2006.01)

(52) U.S. Cl. ...................................... 600/552

(58) Field of Classification Search .................. 600/300, 600/301, 555, 557, 552, 587, 553, 554, 38; 128/898, 904, 920, 903, 892, 894; 601/15, 601/49, 57, 64, 23; 702/19, 139, 41; 705/1; 435/6, 29; 340/541, 540, 568.1, 665, 666, 340/686.1; 361/170, 189; 73/865.4; 307/116, 307/119; 607/138, 96, 2, 62
See application file for complete search history.

(56) References Cited

U.S. PATENT DOCUMENTS

| | | | | |
|---|---|---|---|---|
| 5,429,585 A | * | 7/1995 | Liang | 601/15 |
| 5,673,703 A | * | 10/1997 | Fisher et al. | 600/552 |
| 6,409,685 B1 | * | 6/2002 | Merzenich et al. | 600/587 |
| 6,515,586 B1 | * | 2/2003 | Wymore | 340/541 |
| 6,692,436 B1 | * | 2/2004 | Bluth et al. | 600/300 |
| 6,741,895 B1 | * | 5/2004 | Gafni et al. | 607/138 |
| 7,097,622 B2 | * | 8/2006 | Bleustein et al. | 600/555 |
| 2004/0173220 A1 | * | 9/2004 | Harry et al. | 128/892 |
| 2005/0075669 A1 | * | 4/2005 | King | 607/2 |
| 2005/0124910 A1 | * | 6/2005 | Gupta | 600/552 |
| 2007/0010860 A1 | * | 1/2007 | Gafni et al. | 607/96 |
| 2007/0254288 A1 | * | 11/2007 | Woolf et al. | 435/6 |

* cited by examiner

*Primary Examiner*—Max Hindenburg
*Assistant Examiner*—Brian Szmal
(74) *Attorney, Agent, or Firm*—Cool Patent, P.C.; Joseph P. Curtin

(57) ABSTRACT

Briefly, in accordance with one or more embodiments, a peripheral neuropathy monitor may be incorporated into a scale form factor or other device for monitoring a trend towards peripheral neuropathy by a monitored user or patient. The peripheral neuropathy monitor may include a heating element, a cooling element, and/or a vibrating element, and may be capable of performing the sensitivity of the user to hot, cold, and/or vibrations, and monitor such trends over time to facilitate detecting the onset of peripheral neuropathy. The peripheral neuropathy monitor may be capable of communicating with a remote device via a wired or wireless network for operating the monitor, and for storing and/or analyzing the test results.

13 Claims, 3 Drawing Sheets

PERIPHERAL NEUROPATHY DETECTION

BACKGROUND

Patients with certain diseases may suffer from peripheral neuropathy. Such diseases may include, for example, diabetes and autoimmune diseases such as rheumatoid arthritis and lupus. Certain vitamin deficiencies, some medications and alcoholism can also cause damage in peripheral nerves. In patients suffering from peripheral neuropathy, minor cuts and infections become hard for the patient to detect, and can progress to dangerous levels, leading to expensive treatments and even amputation of the limb in severe cases. Tests have been developed to determine the patient's level of sensation. Some tests involve measuring pain, temperature sensitivity, and vibration sensitivity. These types of tests are generally conducted by trained medical professionals, and require the patient to go to a medical office/clinic or have a home visit.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

Figure 1:
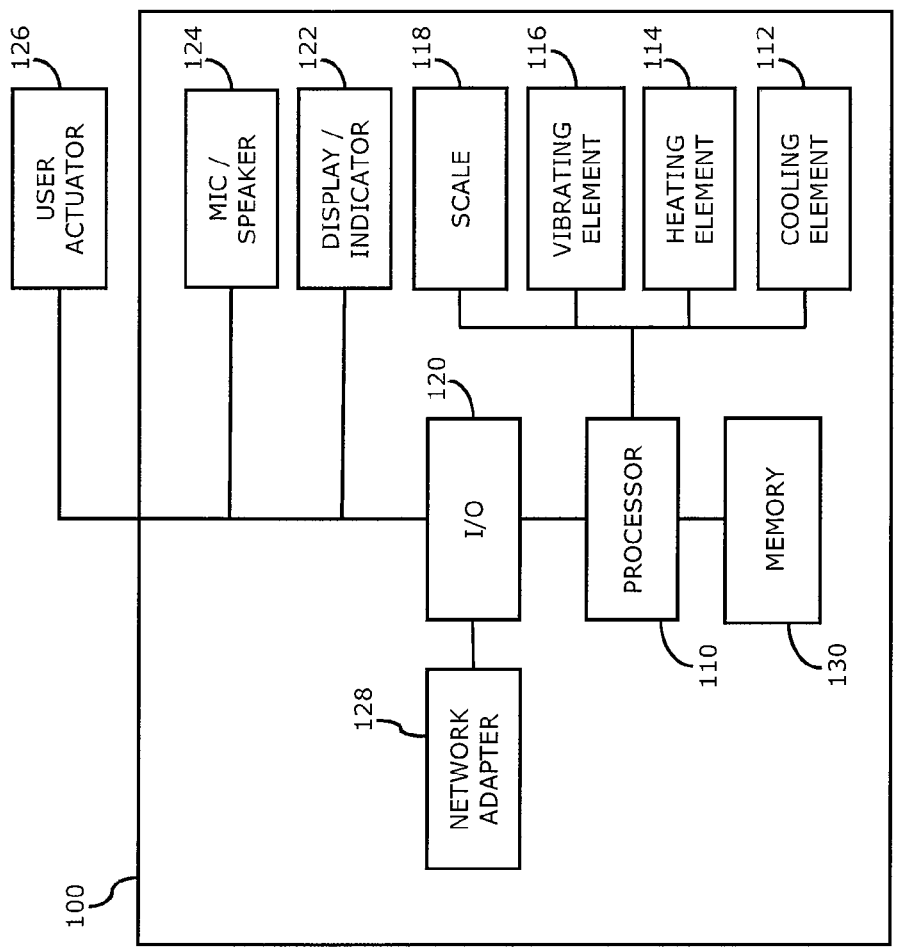
FIG. 1 is a block diagram of a peripheral neuropathy monitor in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. However, "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

Referring now to FIG. 1, a block diagram of a peripheral neuropathy monitor in accordance with one or more embodiments will be discussed. In one or more embodiments, neuropathy monitor 100 may be incorporated into a stand alone device or appliance having approximately the same form factor as a weight scale used for obtaining the weight of a user. In one or more embodiments, neuropathy monitor 100 may be combined with a weight scale in a combination type device. In one or more embodiments, neuropathy monitor 100 may have a weight scale form factor to allow a user or patient to stand on neuropathy monitor 100 and contact a surface of the housing of with one foot or both feet, typically while not wearing shoes or socks. Neuropathy monitor 100 may include a processor 110 coupled to a memory 130, wherein the processor is capable of controlling one or more subsystems, including for example a cooling element 112, heating element 114, vibrating element 116, and/or a weight scale 118. Processor 110 may comprise a basic controller, or a general purpose processor having one or more cores. Heating element 114 may comprise a thermal electric heater or heat coil capable of producing heat in response to an electric current. Likewise, cooling element 112 may comprise a thermal electric cooling element, or Peltier cooler, that is capable of removing heat in response to an electric current. Processor 110 may further couple to an input/output (I/O) subsystem 120 for providing output and/or for receiving input for the control and operation of neuropathy monitor 100. For example, neuropathy monitor 100 may include a display and/or indicator 122 for displaying data regarding the operation of neuropathy monitor 100. Display 122 may comprise a digital display, for example to provide a digital weight reading obtained by scale 118. I/O subsystem 120 may further couple to a microphone and/or speaker 124, for example to receive audio control input from a user where neuropathy monitor 100 is capable of being voice controlled and/or receiving voice input. Likewise, neuropathy monitor 100 may include a speaker to provide audible instructions, information, and/or feedback to a user. Neuropathy monitor 100 may also include a user actuator 126, which may comprise one or more buttons or keys disposed within the housing of neuropathy monitor, and/or may comprise a remote control device having one or more buttons or keys where the remote control device is capable of coupling with neuropathy monitor 100 via a wired or a wireless link such as a Bluetooth link, although the scope of the claimed subject matter is not limited in this respect. Optionally, user actuator 126 may also include a microphone and/or speaker 126, although the scope of the claimed subject matter is not limited in this respect.

In one or more embodiments, neuropathy monitor 100 may include one or more subsystems utilized to monitor a peripheral neuropathy condition of a user, and accompanying code or software executed by processor 110. Heating element 114 and/or cooling element 112 may be utilized to apply heat and/or to cool the foot of the user. At least one thermocouple may be utilized to couple heating element 114 and/or cooling element 112 to the foot of a user to test the temperature sensation of the user to hot and cold temperatures. In one or more embodiments, the thermocouples can be applied to the foot by raising and lowering the thermocouples as needed during temperature testing of the user. The thermocouples may couple heating element 114 and/or cooling element 112 to a metal plate disposed in the housing of neuropathy monitor 100 wherein the user may touch the metal plate with at least part of the foot, toe, or other appendage. Likewise, vibrating element 116 may be utilized to generate vibrations in neuropathy monitor 100 that are capable of being modulated in frequency and/or amplitude. In one or more embodiments, neuropathy monitor 100 is capable of coupling the vibrations generated by vibrating element 116 to a human extremity of the user. For example as discussed, above, neuropathy monitor 100 may comprise a weight scale or similar form factor to couple vibrations from vibrating element to the user's foot or feet. Alternatively, neuropathy monitor 100 may comprise a separate box not having a scale, or may be built into a glove, wristband, boot, sock, and so on, to be capable of monitoring the neuropathy of a peripheral appendage or the like of the user, although the scope of the claimed subject matter is not limited in this respect.

In one or more embodiments, neuropathy monitor 100 may provide one or more methods or mechanisms for the user to indicate whether the user feels the heat or cold, and the magnitude of the heat or cold, and/or at which point the user can no longer feel one or more generated vibrations. For example, the user may actuate a button or key disposed on the housing of neuropathy monitor or alternatively disposed on user actuator 126 where user actuator 126 comprises a remote control or similar device. Likewise, user actuator 126 may comprise a pressure sensor disposed in or on the housing of neuropathy monitor to detect when the user removes one foot or both feet from housing, or steps off of scale 118. Furthermore, the user may provide such input to neuropathy monitor 100 via a microphone disposed in microphone/speaker 124, which may be disposed in or on the housing of neuropathy monitor, and/or disposed in or on an external user actuator. Such a microphone may be utilized to detect the voice of the user, for example by having the user speak what sense the user is detecting, such as something, "cold", "hot" "nothing", "now", and so on, although the scope of the claimed subject matter is not limited in this respect.

In one or more embodiments, neuropathy monitor 100 may have the ability to adapt the temperature, vibration frequencies, initial amplitude, and/or amplitude decay rate into a predetermined pattern or test. For example, during the course of a week, a neuropathy test is run each day by neuropathy system 100, neuropathy system 100 may output a different temperature, frequency and/or initial amplitude of vibration on each day. Such a test pattern may be random or alternatively set along a fixed pattern or set based at least in part on the time measured the previous day.

In one or more embodiments, neuropathy monitor 100 includes processor 110 to conduct one or more neuropathy tests and to control heating element 114, cooling element 112, and/or vibrating element 116, and/or to receive and process data obtained from the user including one or more results of the tests. Alternatively, neuropathy monitor 100 may be controlled by a computer or information handling system disposed externally to neuropathy monitor 100 and which may be coupled to neuropathy monitor 100 via a wired or wireless connection, via I/O subsystem, for example via a Universal Serial Bus (USB) cable or Bluetooth connection, or coupled to the information handling system 100 via network adapter 128, for example via an Ethernet connection, a wireless local area network (WLAN) compliant with an Institute of Electrical and Electronics Engineers (IEEE) 802.11a/b/g/n standard, or the like. Furthermore, neuropathy monitor 100 may be controlled by a remote information handling system 100 coupled to neuropathy monitor 100 via a network such as the internet via network adapter 128, although the scope of the claimed subject matter is not limited in this respect. Such a remote network connection may comprise a mechanism by which data obtained by neuropathy monitor 100 may be transferred to a remote data base such as an Electronic Medical Record data base or other external database from which one or more selected neuropathy tests may be run and in which the results of one or more neuropathy tests may be stored and/or analyzed, although the scope of the claimed subject matter is not limited in this respect. An example of such a remote connection to neuropathy monitor 100 is shown in and described with respect to FIG. 2, below.

Figure 2:
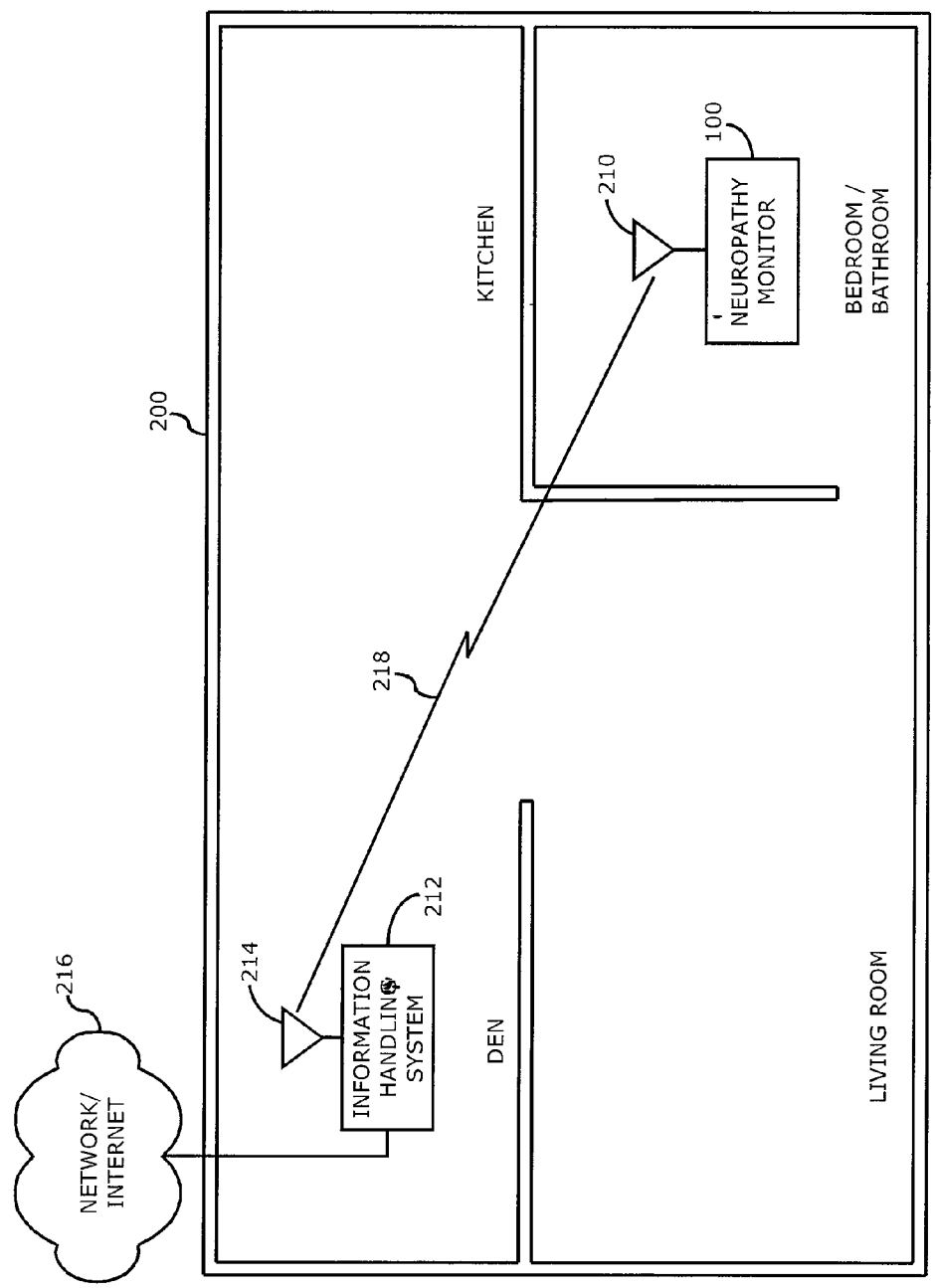
FIG. 2 is a diagram of a house or a similar building in which the peripheral neuropathy monitor of FIG. 1 may be deployed in accordance with one or more embodiments.

Referring now to FIG. 2, a diagram of a house or the similar building in which the neuropathy monitor of FIG. 1 may be deployed in accordance with one or more embodiments will be discussed. As shown in FIG. 2, neuropathy monitor 100 may be deployed in the home 200 of a user, for example in a bedroom and/or in a bathroom. In one or more embodiments, neuropathy monitor 100 may include a network adapter 128 and appropriate antenna 210 that is capable of communicating wirelessly via wireless link 218 to a remote information handling system 212 likewise having an antenna 214. Alternatively, neuropathy monitor 100 may couple to information handling system 212 via a wired link such as an Ethernet type connection or the like. As shown in FIG. 2, neuropathy test data obtained by neuropathy monitor 100 may be transmitted to information handling system 212 for storage and/or analysis of the test data. In one particular embodiment, information handling system 212 may be capable of analyzing the test data obtained by neuropathy monitor 100 and flagging a test result that may indicate that the user may be suffering from peripheral neuropathy. Flagging may generally refer to the highlighting or otherwise indicating of a test score that may be indicative of peripheral neuropathy for example so that a medical professional may follow up and review the test result. Such a flag may be stored at least temporarily in information handling system 212 that may be later retrieved by a medical professional who periodically visits home 212. Alternatively, information handling system 212 may provide a print out of the test results, including a flag of one or more tests if so indicated, so that the user may take the print out to a medical professional for review and diagnosis. In one particular embodiment, information handling system 212 is capable of running a diagnosis program, for example using artificial intelligence or the like, to infer and/or diagnose a condition of the user based at least in part on one or more test results. Furthermore, information handling system 212 is capable of coupling to a remote device or system via network 216, which may comprise the internet, to where the remote device or system, or a medical professional operating the remote device or system, may be capable of analyzing the test results and/or diagnosing a condition of the user based at least in part on the test results obtained by neuropathy monitor 100.

Likewise, neuropathy monitor 100 may have its own capabilities similar to those of information handling system 212. For example, neuropathy monitor 100 may be adapted to controlling the elements and performing one or more tests, however more advanced processing may be performed by information handling system 100. In another embodiment, neuropathy monitor 100 may include more advance processing and adaptive learning based at least in part on one or more test results from previously run tests. In such an embodiment, such tests may be fixed, that is selected from a group of predetermined tests stored in neuropathy monitor 100, or alternatively the tests may be adaptive in that a test that is run one day may be based on one or more tests that were run on one or more previous days or times. For example, if a previous test indicates that the user may be trending toward peripheral neuropathy, the next test run by neuropathy monitor 100 may be a more thorough test to obtain greater precision in the test results. In yet another embodiment, processor 110 may be capable of executing more advanced code or software that is capable of inferring and/or diagnosing a peripheral neuropathy status of the user based on an analysis of one or more test results obtained by neuropathy monitor 100. However, these are merely examples of how neuropathy monitor 100, information handling system 212, and/or a remote device coupled to neuropathy monitor 100 and/or information handling system 212, or a medical professional using such equipment, may be able to operate neuropathy monitor 100, conduct one or more neuropathy tests, and/or to analyze or diagnose a condition of the user based on one or more test results, and the scope of the claimed subject matter is not limited in this respect.

In one or more embodiments, neuropathy monitor 100 may be capable of conducting one or more peripheral neuropathy tests to monitor and/or identify progression of the user towards peripheral neuropathy over time. For example, a person suffering from peripheral neuropathy may gradually lose the ability to sense heat and/or cold in his or her extremities. Likewise, a user suffering from peripheral neuropathy may also gradually lose the ability to sense vibrations. Typically, a user may lose temperature sensation before losing vibration sensation. Neuropathy monitor 100 may apply a predetermined temperature to the metal plate of the housing that is touched by the user. The user may then be prompted by neuropathy monitor for a response indicating how hot or how cold the user perceives the output to be. For example, the user may be asked via microphone/speaker 124 the level of heat or cold sensed by the user on a scale of 1 to 10. Such a query may comprise voice synthesized speech or prerecorded speech. The user may provide feedback to neuropathy monitor 100 by entering the number between 1 and 10 via user actuator 126. Alternatively, the user may speak the number and the user's voice data may be obtained by microphone 124, and optionally processed to determine the spoken number or stored as an audio file. In another embodiment, the user may actuate a button on user actuator 126 in response to the user detecting the output of neuropathy monitor 100. The tests may alternate from day to day, with cold being tested on one day and heat being tested on another day so that user bias may be eliminated from the test results. Likewise, the level of heat and/or cooling may be varied from day to day to determine a level of temperature sensitivity of the user. Randomness in the testing may also be provided to help ensure the accuracy of the test results.

In one or more embodiments, neuropathy monitor 100 may be capable of conducting one or more vibration sensitivity tests to measure changes in sensation by the user to vibrations. As with temperature testing described above, neuropathy monitor 100 may generate a vibration having a selected amplitude and/or frequency via vibrating element 116. The frequency of the vibrations may run from as low as about 60 Hertz to about 300 or 400 Hertz in one or more embodiments. In general, the frequency may range from the tens of Hertz to the hundreds of Hertz. Neuropathy monitor 100 may test a different frequency from test to test or day to day, or the frequency may be gradually increased from a lower frequency to a higher frequency during the test, or from a higher frequency to a lower frequency. The user may actuate user actuator 126 when the user can detect vibration at the tested frequency. Likewise, the amplitude of the vibrations may be increased from a lower amplitude to a higher amplitude, or from a higher amplitude to a lower amplitude. The user may then actuate user actuator 126 in response to detecting a threshold amplitude and/or frequency. In one or more embodiments, the tests performed by neuropathy monitor 100 may be basic tests capable of testing temperature and/or vibration sensitivity of the user in order to detect progression of the user towards peripheral neuropathy. Such tests may be utilized to indicate a trend towards peripheral neuropathy, without necessarily providing detailed testing or analysis. In one or more embodiments, neuropathy monitor 100 may be capable of performing more detailed and more advanced tests, for example in response to a detected trend towards peripheral neuropathy and/or in response to an order from a physician or other medical professional. However, these are merely example tests capable of being performed by neuropathy monitor 100, and the scope of the claimed subject matter is not limited in this respect.

Figure 3:
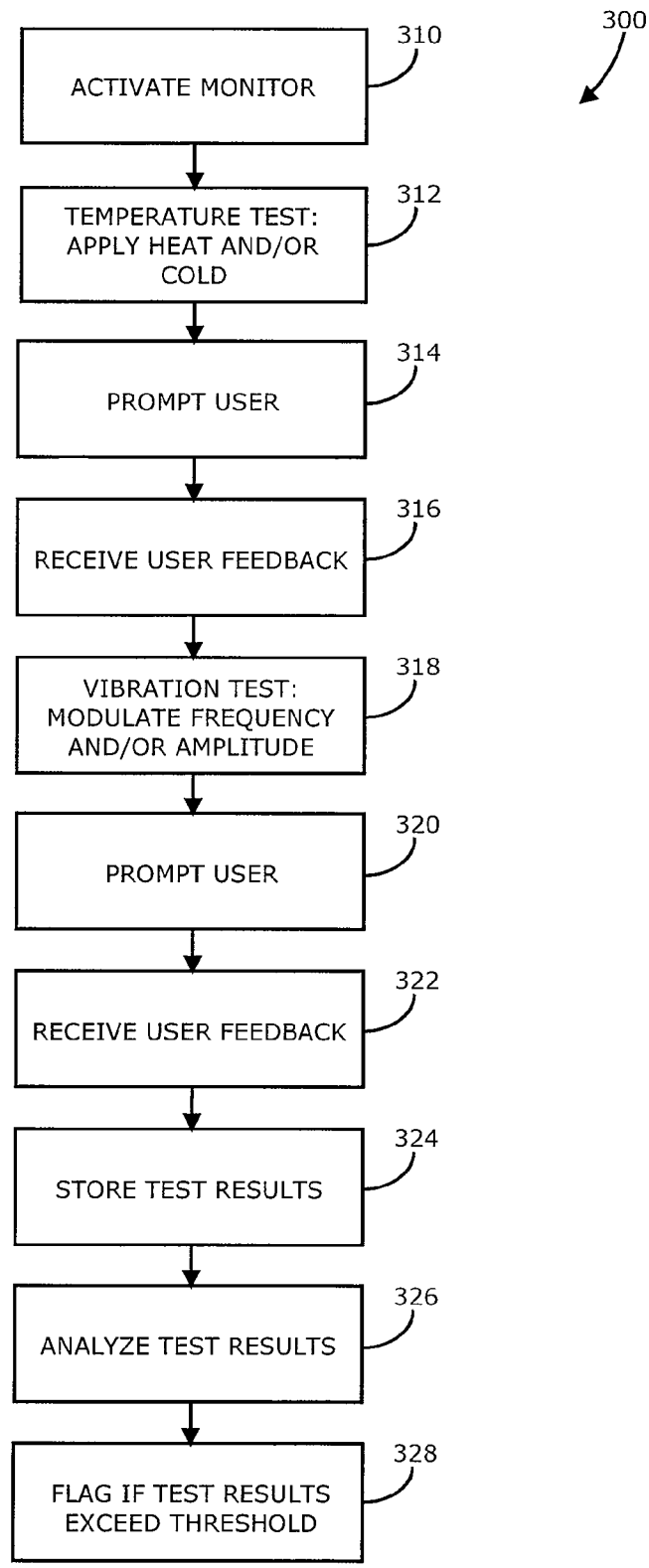
FIG. 3 is a flow diagram of a method for monitoring peripheral neuropathy in accordance with one or more embodiments.

FIG. 3 is a flow diagram of a method for monitoring peripheral neuropathy in accordance with one or more embodiments. Method 300 may be executed by neuropathy monitor 100, for example via code or software executed by processor 110 and/or by information handling system 212, and may include more blocks or fewer blocks than shown, and/or the other orders of the blocks of method 300 may be implemented, and the scope of the claimed subject matter is not limited in this respect. Neuropathy monitor 100 may be activated at block 310, for example in response to the user stepping on the top surface of neuropathy monitor 100 where the form factor is a weight scale or the like. For example, if neuropathy monitor 100 detects a weight greater than a predetermined threshold, such as at or near the weight of the user, or if the detected weight is a non-zero weight, as detected by scale 118, neuropathy monitor 100 may be activated and one or more neuropathy tests may be initiated. In some embodiments, neuropathy monitor 100 may be designed to be operated by the user while the user is sitting, in which case a threshold weight to activate neuropathy monitor may be a percentage of the known or expected weight of the user, for example at approximately a weight of 15% of the user's weight. A temperature test may be executed at block 312, for example to test the sensitivity of the user to cold and/or heat, by actuating heating element 114 and/or cooling element 112. The user may then be prompted at block 314 for a response to the test, for example if the user can detect the hot or cold output, and/or a level of hot or cold detected by the user. Neuropathy monitor 100 may receive the user's feedback at block 316, for example via user actuator 126 and/or the microphone of microphone/speaker 124. Likewise, neuropathy monitor 100 may perform one or more vibration tests at block 318 at which a vibration may be provided by vibrating element 116, where the frequency and/or amplitude of the vibration may be modulated according to the particular test being performed. The user may be prompted at block 320 for the user's response to the vibration test, and the user's feedback may be received at block 322, for example via user actuator 126 and/or the microphone of microphone/speaker 124. After performing one or more tests, neuropathy monitor 100 may store one or more test results in a memory or hard drive of neuropathy monitor 100, or alternatively in a memory or hard drive of information handling system 212 or of a remote device or system coupled to network 216. The test results may be analyzed at block 326, for example to determine any trend or pattern indicating that the user may be suffering from peripheral neuropathy. If it is determined that the user may be trending towards or suffering from peripheral neuropathy based at least on one or more tests, such a result may be flagged at block 328 of the test results exceed a threshold of a normal range of sensitivity. For example, display/indicator 122 of neuropathy monitor 100 may display a visual flag to the user so that the user is aware of the flag. Alternatively, the flag may be transmitted to information handling system 212 for storage in information handling system 212 and/or indicated in a report stored in information handling system 212. In another alternative, the flag may be transmitted to a remote device or system coupled to network 216 for entry into a medical record of the user and/of for review by a medical professional monitoring the user by operating the remote device or system.

Although the claimed subject matter has been described with a certain degree of particularity, it should be recognized that elements thereof may be altered by persons skilled in the art without departing from the spirit and/or scope of claimed subject matter. It is believed that the subject matter pertaining to peripheral neuropathy detection and/or many of its attendant utilities will be understood by the forgoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. An apparatus, comprising:
   a housing;
   a vibrating element disposed in the housing, the vibrating element being capable of producing a vibration at a selected frequency and amplitude;
   a temperature element disposed in the housing and being capable of producing thermal output at a selected temperature;
   a scale element disposed in the housing, the scale element comprising a weight scale form factor wherein the user stands on the housing during operation of the apparatus by the user, and the scale element being capable of detecting a non-zero weight of the at least part of the user when the user stands on the housing during operation of the apparatus,
   a processor disposed in the housing, the processor being capable of controlling the vibrating element and the temperature element, individually or in combination, to run one or more peripheral neuropathy tests on an extremity of a user that is coupled with the vibrating element or the temperature element, or a combination thereof, in response to a non-zero weight being detected by the scale element;
   a user actuator to provide user feedback to the processor in response to the one or more neuropathy tests on the extremity of the user; and
   a memory disposed in the housing, the memory being coupled to the processor to store results of the one or more neuropathy tests and the user feedback received via the user actuator;
   wherein the processor is further capable of processing the one or more neuropathy tests for detecting a trend towards peripheral neuropathy of the extremity of the user, and in response to a detected trend towards peripheral neuropathy of the extremity of the user, the processor further capable of adaptively learning and selecting one or more neuropathy tests from a group of predetermined stored neuropathy tests and controlling the vibrating element and the temperature element, individually or in combination, to run the one or more selected peripheral neuropathy tests on the extremity of the user, the one or more selected neuropathy tests being selected based at least in part on the results of one or more previous neuropathy tests on the extremity of the user and the user feedback stored in the memory to further identify progression of the peripheral neuropathy of the extremity of the user over time.

2. An apparatus as claimed in claim 1, said temperature element comprising a heating element or a cooling element, or a combination thereof.

3. An apparatus as claimed in claim 2, further comprising a speaker and said user actuator comprising a microphone, said microphone to provide user feedback to the processor in response to the one or more neuropathy tests and the speaker to provide audio information to the user.

4. An apparatus as claimed in claim 3, further comprising a wireless network adapter coupled to the processor, said wireless network adapter being capable of communicating with a remote device, wherein the remote device is capable of storing test results of the one or more neuropathy tests, or controlling the one or more neuropathy tests, or combinations thereof.

5. An apparatus according to claim 4, wherein the extremity of the user comprises at least part of one or more feet or at least part of a toe, or a combination thereof.

6. A method, comprising:
   activating a peripheral neuropathy monitor in response to detecting actuation of a user actuator by a user, the actuation of the user actuator being based at least in part on detecting a weight of a user, or a partial weight of a user, upon a surface of a device housing;
   performing one or more peripheral neuropathy tests on an extremity of the user by the peripheral neuropathy monitor in response to said activating, the one or more peripheral neuropathy tests on the extremity of the user comprising a vibration test, and a heat test, or a cold test, or combinations thereof;
   prompting the user for a response to the one or more peripheral neuropathy tests;
   storing the response to the one or more peripheral neuropathy tests as a neuropathy test result;
   processing the neuropathy test result;
   detecting a trend toward peripheral neuropathy of the extremity of the user based on the processed neuropathy test result; and
   in response to the detected trend towards peripheral neuropathy of the extremity of the user, the peripheral neuropathy monitor adaptively learning and selecting one or more neuropathy tests from a group of predetermined stored neuropathy tests that are subsequently performed on the extremity of the use based at least in part on the processed neuropathy test results to further identify progression of the peripheral neuropathy of the extremity of the user over time.

7. A method as claimed in claim 6, said performing further comprising applying heat or cold to the extremity of the user at a selected temperature, and said prompting further comprising requesting the user to rate the level of heat or cold applied to the extremity of the user on a numerical scale.

8. A method as claimed in claim 7, said performing further comprising randomly performing the vibration test and the heat test, or the cold test, or combinations thereof.

9. A method as claimed in claim 8, said performing further comprising performing a current test based at least in part on the results from one or more previous tests.

10. A method as claimed in claim 9, said performing further comprising applying a vibration to the extremity of the user at selected frequency and amplitude, and gradually increasing the amplitude or frequency of the vibration or combinations thereof until the user is able to detect the vibration, or gradually decreasing the amplitude or frequency of the vibration or combinations thereof until the user is no longer able to detect the vibration.

11. A method as claimed in claim 10, further comprising analyzing the test result to determine if the extremity of the user is trending toward peripheral neuropathy, and if so highlighting the test result for follow up.

12. A method according to claim 11, wherein the extremity of the user comprises at least part of one or more feet or at least part of a toe, or a combination thereof.

13. A method as claimed in claim 10, further comprising transmitting the test result to a remote device for storage or analysis, or combinations thereof.

* * * * *

UNITED STATES PATENT AND TRADEMARK OFFICE
CERTIFICATE OF CORRECTION

| | | |
|---|---|---|
| PATENT NO. | : 7,854,703 B2 | Page 1 of 1 |
| APPLICATION NO. | : 11/860846 | |
| DATED | : December 21, 2010 | |
| INVENTOR(S) | : David Poisner | |

It is certified that error appears in the above-identified patent and that said Letters Patent is hereby corrected as shown below:

In Column 8, line 56, in Claim 6, delete "use" and insert -- user --, therefor.

Signed and Sealed this
Twelfth Day of April, 2011

David J. Kappos
*Director of the United States Patent and Trademark Office*